US011160547B2

(12) United States Patent
Demir

(10) Patent No.: US 11,160,547 B2
(45) Date of Patent: Nov. 2, 2021

(54) SUTURES AND SUTURING TECHNIQUES

(71) Applicant: Resit Demir, Nuremberg (DE)

(72) Inventor: Resit Demir, Nuremberg (DE)

( * ) Notice: Subject to any disclaimer, the term of this patent is extended or adjusted under 35 U.S.C. 154(b) by 569 days.

(21) Appl. No.: 15/940,144

(22) Filed: Mar. 29, 2018

(65) Prior Publication Data

US 2019/0298335 A1 Oct. 3, 2019

(51) Int. Cl.
*A61B 17/04* (2006.01)
*A61B 17/00* (2006.01)

(52) U.S. Cl.
CPC ...... *A61B 17/0469* (2013.01); *A61B 17/0401* (2013.01); *A61B 17/0482* (2013.01); *A61B 2017/00663* (2013.01); *A61B 2017/0496* (2013.01)

(58) Field of Classification Search
CPC ............ A61B 17/0469; A61B 17/0482; A61B 17/0401; A61B 2017/00663; A61B 2017/0496; A61B 17/06166
See application file for complete search history.

(56) References Cited

U.S. PATENT DOCUMENTS 9,084,598 B2 * 7/2015 Fedinec .................. D04C 1/12
2012/0071903 A1 * 3/2012 Knoell ............. A61B 17/06166
606/148

OTHER PUBLICATIONS

Jacobus W. A. Burger, Md, Roland W. Luijendijk, Ph.D., Wim C. J. Hopp, Ph.D., Jens A. Halm, Md, Emiel G. G. Verdaasdonk, Md, and Johannes Jeekel, Ph.D.; Long-term Follow-up of a Randomized Controlled Trial of Suture Versus Mesh Repair of Incisional Hernia; Annals of Surgery; vol. 240, No. 4, Oct. 2004.
C. Fink, P. Baumann, M.N. Wente, P. Knebel, T. Bruckner, A. Ulrich, J. Werner, M.W. Buchler and M. K. Diener; "Incisional hernia rate 3 years after midline laparatomy"; Published by John Wiley & Sons Ltd, 2013; 101: 51-54.
Volker Schumpelick; Georg Arlt; Uwe Klinge; "Versorgung von Nabelhernie und Narbenhernie"; Deutsche Arzteblatt 94, Heft 51-52, Dec. 22, 1997.

* cited by examiner

*Primary Examiner* — Elizabeth Houston
*Assistant Examiner* — Michael G Mendoza
(74) *Attorney, Agent, or Firm* — Hartman Global IP Law; Gary M. Hartman; Domenica N.S. Hartman

(57) ABSTRACT

Suturing techniques and sutures capable of reducing the incidence of incisional herniae, including but not limited to subcutaneous surgical sutures performed after laparotomy. Such a suture includes a circular suture having at least first portions that are within a first region of tissue of a suture area that further contains rows of puncture sites aligned approximately parallel to an incision on opposite sides of the incision. The first region of tissue is located between the rows of puncture sites and surrounds the incision, and the first portions of the circular suture extend along the rows of puncture sites. The suture further includes a continuous suture in the suture area that penetrates the puncture sites and traverses the incision. The circular suture disperses stresses induced by tension in the continuous suture to inhibit tearing of tissue at the puncture sites.

11 Claims, 3 Drawing Sheets

SUTURES AND SUTURING TECHNIQUES

BACKGROUND OF THE INVENTION

The present invention generally relates to suturing openings or wounds of a living body. The invention particularly relates to suturing techniques that can be performed after laparotomy to reduce the incidence of incisional herniae (hernias).

Laparotomy (also known as celiotomy) is a surgical procedure that involves making a relatively large incision through the abdominal wall, typically a midline incision through the fascia along the linea alba, to gain access into the abdominal cavity. A subcutaneous surgical suture is often employed to close the incision. An incidence of approximately 2 to 20% of incisional hernia post laparotomy has been reported. In the U.S.A., approximately four to five million laparotomies are performed each year and as such approximately 500,000 cases of incisional hernia may occur each year, of which 200,000 will likely need to be surgically repaired (Burger et al., 2004). In Germany, one can expect 40,000 to 70,000 cases of incisional hernia per year. The approximate costs associated with surgical repair per patient is approximately 5,000 to 10,000 € which accounts for total annual costs of up to 700 million € (Schumpelick et al., 1997).

Two techniques are commonly used to suture the abdominal wall: continuous sutures and simple interrupted sutures. The surgeon may choose resorbing or non-resorbing suture materials. For the resorbing materials there are different time scales for the resorption (the common differentiating factor is half-life).

Despite progress in the development of novel suture materials and efforts to advance existing suturing techniques, there has been no major improvement of the incidence of incisional hernia after primary wound closure over the last decades (Fink et al., 2013). Numerous clinical trials have disproved the desired effects of developing and using novel suture materials.

In view of the above, it can be appreciated that there are certain disadvantages associated with prior art suturing techniques performed post laparotomy, and that it would be desirable if suturing techniques were available that were capable of overcoming or avoiding certain disadvantages noted above.

BRIEF DESCRIPTION OF THE INVENTION

The present invention provides suturing techniques and sutures capable of reducing the incidence of incisional herniae, including but not limited to subcutaneous surgical sutures performed after laparotomy.

According to one aspect of the invention, a suturing technique is provided that involves closing an opening defined by opposing edges of an incision in tissue of a living body. The technique includes designating a suture area of the tissue that comprises rows of puncture sites aligned approximately parallel to the incision on opposite sides of the incision and a first region of tissue located between the rows of puncture sites and surrounding the incision, using at least a first suture thread to create a circular suture having at least first portions that extend along the rows of puncture sites and are within the first region of tissue, and using at least a second suture thread to create a continuous suture in the suture area that penetrates the puncture sites and traverses the incision.

According to another aspect of the invention, a suture is provided that closes an opening defined by opposing edges of an incision in tissue of a living body. The suture includes a circular suture having at least first portions that are within a first region of tissue of a suture area that further comprises rows of puncture sites aligned approximately parallel to the incision on opposite sides of the incision. The first region of tissue is located between the rows of puncture sites and surrounds the incision, and the first portions of the circular suture extend along the rows of puncture sites. The suture further includes a continuous suture in the suture area that penetrates the puncture sites and traverses the incision.

A technical aspect of techniques and sutures as described above includes the ability of the circular suture to disperse stresses induced by tension in the continuous suture. The circular suture disperses the stresses along the rows of puncture sites to an extent that tearing of the first region of tissue at each of the puncture sites is inhibited.

Other aspects and advantages of this invention will be further appreciated from the following detailed description.

DETAILED DESCRIPTION OF THE INVENTION

The invention relates to suturing techniques that use needles and suture threads to close openings and wounds defined by opposing edges of tissue of a living body. Preferred aspects of suturing techniques described herein include, but are not limited to, the ability to reduce the incidence of incisional hernia after laparotomy, in which case a subcutaneous surgical suture is often used to close a relatively large incision that was made in the fascia of the abdominal wall to gain access to the abdominal cavity.

The suturing techniques described below were developed as a result of thorough investigative analysis of cases of post laparotomy incisional herniae, from which it was concluded that, though suture threads are capable of retaining the fascia, herniae were caused by the adjacent tissue of the fascia slowly tearing at the point of maximum stress in the abdominal wall. As such, it was concluded that to avoid incisional herniae, there is a need for a suturing technique that prevents or at least inhibits the fascia from tearing at the puncture sites. Investigations leading to the present invention evidenced that tearing of the fascia at puncture sites can be inhibited by dispersing stresses across the entire length of the suture line, and in particular by introducing a stress component parallel to the suture line in order to disperse stress across axes that are parallel and perpendicular to the suture line. Suturing techniques developed as a result can be applied in cases of primary fascial closure after laparotomy, as well as a variety of other cases including but not limited to umbilical herniae and incisional herniae if a fascial closure without a major increase of intra-abdominal pressure is possible.

Figure 1:
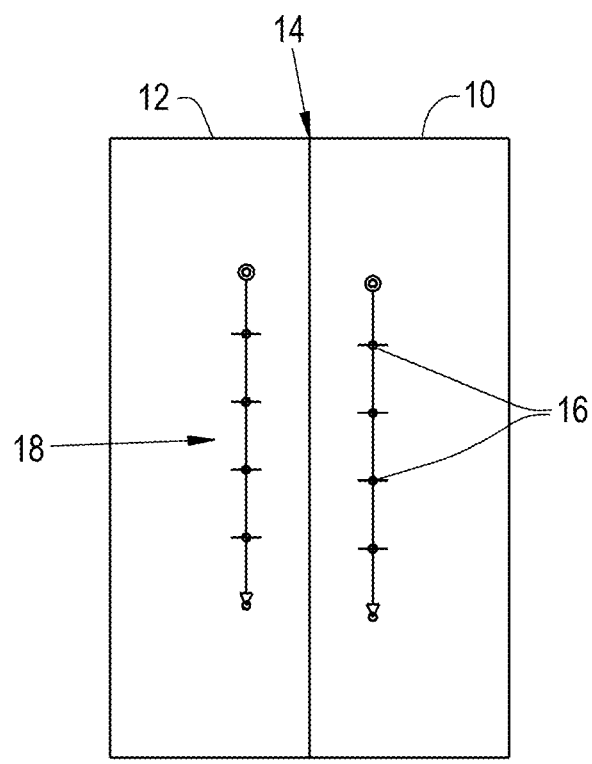
FIG. 1 is an image showing an experimental setup in which two sheets are arranged to have edges thereof abutting each other to simulate edges of an incision.

Suturing techniques described below may be referred to as a "spider suturing technique" to create a "spider suture," referred to as such due to some resemblance to a spider web. Aspects and steps relating to spider suturing techniques will be described in reference to FIGS. 1 through 5. For demonstrative purposes, FIG. 1 is an image showing an experimental setup in which two sheets (paper) 10 and 12 are arranged so that edges of the sheets 10 and 12 abut each other to simulate edges of an incision 14 in tissue, for example, the fascia of an abdominal wall. A pair of roughly parallel lines, one on each sheet 10 and 12, identifies rows of puncture sites 16 in the tissue where one or more suture threads will penetrate the tissue during the suturing procedure. The rows of puncture sites 16 are on opposite sides of the incision 14 and oriented in a direction referred to herein as a parallel direction to the incision 14 and, at the conclusion of the procedure, the suture line. An area over which the suturing technique will be performed, referred to herein as the suture area 18, is defined herein as including the rows of puncture sites 16 and a region of tissue between the rows of puncture sites 16.

Figure 2:
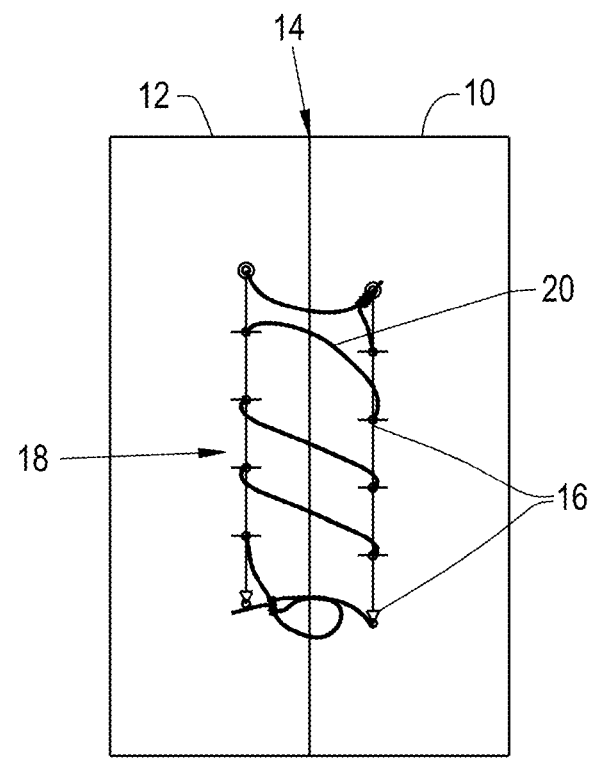
FIG. 2 is an image showing sutures traversing the incision in accordance with a state of the art suturing technique.

In FIG. 2, a state of the art suturing technique is represented in which a suture thread has been placed in the suture area 18 of FIG. 2 to create a continuous suture 20. A needle (not shown) has been used to puncture the sheets 10 and 12 at their respective puncture sites 16, and the suture thread traverses the suture area 18 and incision 14 in directions generally oblique to the parallel direction. One end of the continuous suture 20 (in FIG. 2 the upper end) is fixed with the suture 20 itself, while its other end (in FIG. 2 the lower end) is fixed with a single-button suture, which has been applied for just this purpose. Alternatively, also the lower end of the suture 20 in FIG. 2 could be fixed with itself; or its upper end in FIG. 2 could be fixed with a single-button suture. The suture thread has not been tensioned in FIG. 2 for illustrative purposes. Once tensioned, the suture thread induces stresses in the tissue adjacent each puncture site 16, which if sufficient may slowly tear the tissue and allow an incisional hernia to develop.

Figure 3:
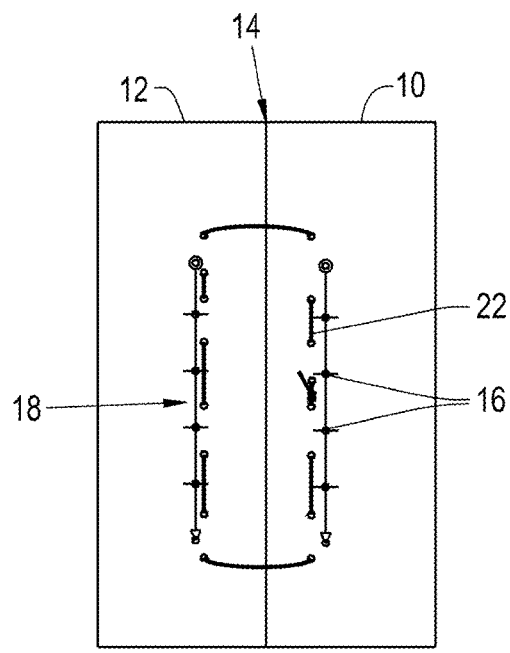
FIG. 3 is an image showing a circular suture performed as part of a basic spider suture in accordance with a nonlimiting embodiment of the invention.

FIG. 3 is an image showing a step in a spider suture technique in accordance with a nonlimiting embodiment of the invention. FIG. 3 represents a continuous circular suture 22 in which a suture thread (which may be referred to herein as a first suture thread or first thread) intermittently penetrates and exits the tissue along each row of puncture sites 16 (i.e., in the parallel direction), while generally avoiding penetration at any of the puncture sites 16. The portions of the circular suture 22 along each row of puncture sites 16 are represented as being interior of the puncture sites 16, in other words, on the side of the row of puncture sites 16 proximal to the incision 14, and therefore entirely within the suture area 18. Other portions of the suture thread bridge the incision 14 at opposite ends of the suture area 18, generally in directions referred to herein as a perpendicular direction to the incision 14 and the resulting suture line at the conclusion of the procedure. The portions of the suture thread bridging the incision 14 are represented as being outside what has been defined herein as the suture area 18. The circular suture 22 is represented in FIG. 3 as a single continuous thread applied to both sides of the incision 14 so as to surround the incision 14 and closed with a single knot. However, it is foreseeable that the circular suture 22 could be created with multiple suture threads.

Figure 4:
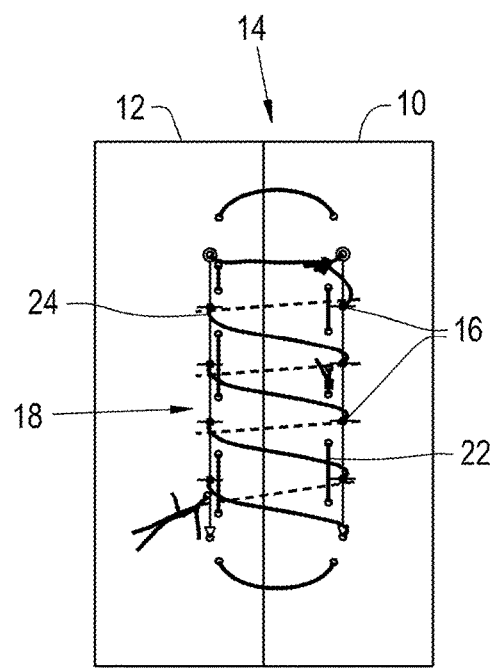
FIG. 4 is an image showing the basic spider suture of FIG. 3 as further comprising a continuous suture with puncture sites outside the circular suture of FIG. 3.

FIG. 4 is an image showing the spider suture of FIG. 3 as further comprising a continuous suture 24 in the suture area 18 that utilizes the puncture sites 16 located outside of the circular suture 22 of FIG. 3. As with standard continuous sutures such as represented in FIG. 2, the continuous suture 24 is formed with a suture thread (which may be referred to herein as a second suture thread or second thread) that successively traverses the incision 14 above the tissue (visible in FIG. 4) and below the tissue (represented by phantom lines in FIG. 4) in transverse directions to the incision 14. The continuous suture 24 is represented in FIG. 4 as a single continuous thread closed with a single knot, though it is foreseeable that the continuous suture 24 could be created with multiple suture threads. Also, one or both ends of the thread of the continuous suture 24 may be fixed to the continuous suture 24 itself or to a single-button suture (for example, similar to that shown in FIG. 2), respectively, wherein the respective single-button suture has been applied for this very purpose. The suture thread shown in FIG. 4 has not been tensioned for illustrative purposes. Once tensioned, the continuous suture 24 induces stresses in the tissue adjacent each puncture site 16.

According to a preferred aspect of the invention, the circular suture 22 introduces a stress component that is parallel to and along the entire length of the suture line so that stresses induced by tension in the continuous suture 24 are dispersed by the circular suture 22 across axes that are parallel to the suture line (e.g., along each row of puncture sites 16 of the continuous suture 24) and approximately perpendicular to the suture line (e.g., along each suture thread of the continuous suture 24 that traverses the incision 14), preferably to the extent that stresses induced by the sutures 22 and 24 are inhibited from tearing the tissue at each puncture site 16.

Figure 5:
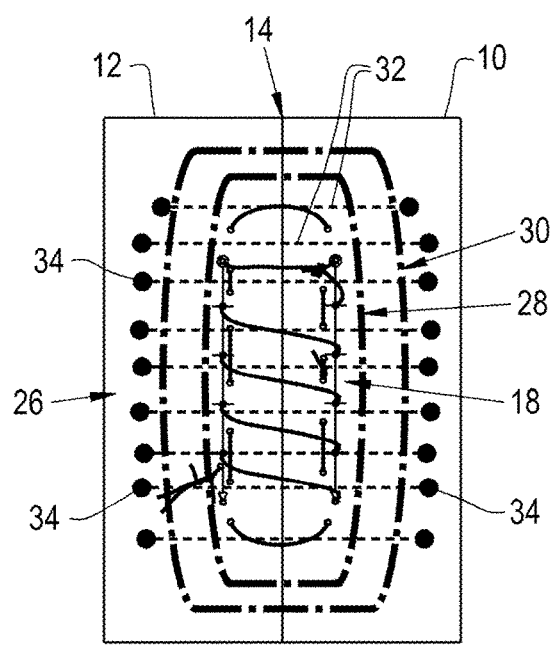
FIG. 5 is an image showing an extended spider suture in accordance with another nonlimiting embodiment of the invention, wherein additional circular sutures and crosslink sutures are present.

Depending on the consistency of the incision 14, the basic spider suture represented in FIG. 4 may be modified by adding one or more additional circular sutures 28 and 30 in expanding circles outside the suture area 18 designated in FIGS. 3 and 4, thereby defining an extended suture area 26 that surrounds the original suture area 18 and its sutures 22 and 24. Additionally, FIG. 5 represents the addition of linear crosslink sutures 32 that may be applied to transversely extend across the incision 14 from two rows of additional puncture sites 34 located at the boundary of the extended suture area 26. Once tensioned, the suture threads of the crosslink sutures 32 induce stresses in the tissue adjacent each puncture site 34, which are inhibited from tearing the tissue as a result of the circular sutures 28 and 30 dispersing stresses along each row of puncture sites 34.

Figure 6:
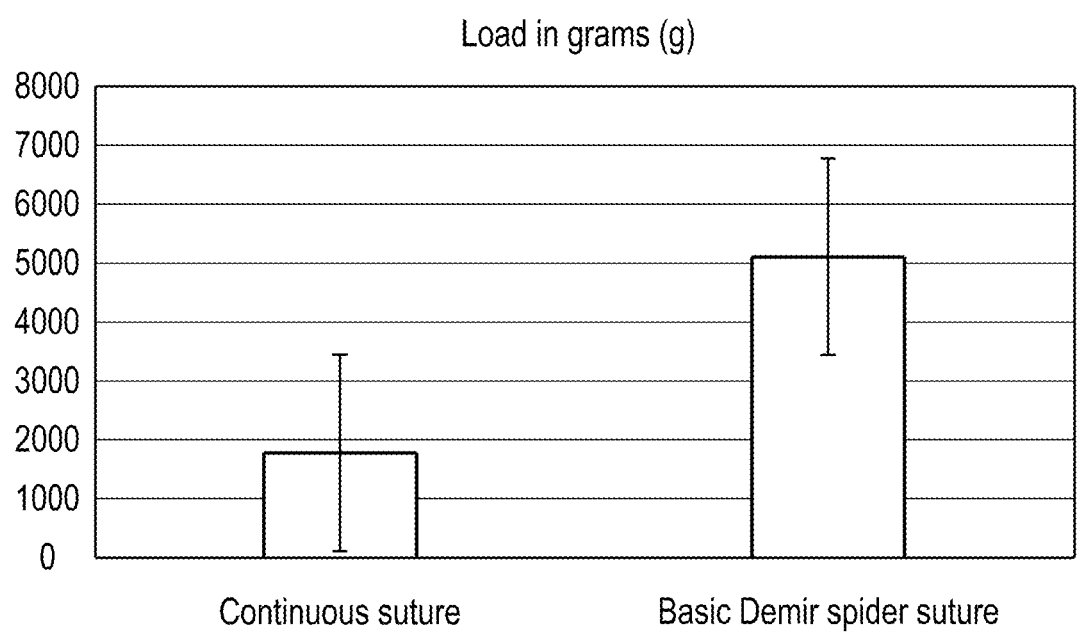
FIG. 6 contains a graph representing tensile results of a test conducted during an experiment leading to the present invention.

An experiment was conducted for the purpose of comparing the carrying capacities of a basic spider suture generally configured as represented in FIG. 4 and a state of the art continuous suture generally configured as represented in FIG. 2. In the experiment, two sheets of paper were sutured at their abutting edges along a length of approximately 5 cm (about 2 inches) with the known technique of FIG. 2 and the spider suture technique of FIGS. 3 and 4. In both cases, monofilament thread ("Resolon 2-0, Resorba") was used. Tension in the perpendicular direction across the incision was applied with a bucket to which sand was added until the sutures tore. The carrying capacities of the two suturing techniques were determined by the final weight of the bucket when the sutures tore. The number of repetitions was five for each suture. FIG. 6 evidences that the spider suture exhibited a significant increase (Fisher's test, p=0.017) of mean carrying capacity over the state of the art continuous suture, specifically, 5101.75 g as compared to 1776.5 g, as tabulated in the table below. These results were concluded to have confirmed that the circular suture utilized by the spider suture technique successfully dispersed stresses along each row of puncture sites of the continuous sutures to the extent that tearing of the suture line was inhibited.

|  | Continuous suture | Basic spider suture |
| --- | --- | --- |
| Carrying capacity in g | 1776.5 | 5101.75 |
| Standard deviation | 169.9 | 975.7 |

While the invention has been described in terms of specific or particular embodiments, it should be apparent that alternatives could be adopted by one skilled in the art. For example, any number of suture threads could be used in the procedure and materials and components employed by the procedure could differ in composition, appearance, and construction from the embodiments described herein and shown in the drawings. As such, it should be understood that the above detailed description is intended to describe the particular embodiments represented in the drawings and certain but not necessarily all features and aspects thereof, and to identify certain but not necessarily all alternatives to the represented embodiments and described features and aspects. Accordingly, it should be understood that the invention is not necessarily limited to any embodiment described herein or illustrated in the drawings. It should also be understood that the phraseology and terminology employed above, including the terms "circular" and "continuous" when describing the sutures 22, 24, 28, and 30, are for the purpose of describing the illustrated embodiments and investigation, and do not necessarily serve as limitations to the scope of the invention. Therefore, the scope of the invention is to be limited only by the following claims.

The invention claimed is:

1. A suturing technique for closing an opening defined by opposing edges of an incision in tissue of a living body, the suturing technique comprising:
    designating a suture area of the tissue that comprises rows of puncture sites in the tissue within the suture area, the rows of puncture sites being aligned approximately parallel to the incision on opposite sides of the incision and a first region of tissue located between the rows of puncture sites and surrounding the incision;
    using at least a first suture thread to create a circular suture that is in the tissue of the suture area, continuous around the incision, and closed with a knot to form a closed loop surrounding the incision, the circular suture having at least first portions that extend along the rows of puncture sites and are within the first region of tissue; and
    using at least a second suture thread to create a continuous suture in the suture area that penetrates the puncture sites and traverses the incision;
    wherein the first and second suture threads form a suture and stresses induced by tension in the continuous suture are dispersed by the circular suture along the rows of puncture sites to an extent that tearing of the first region of tissue at each of the puncture sites is inhibited.

2. The suturing technique according to claim 1, wherein the suture is a subcutaneous suture.

3. The suturing technique according to claim 2, wherein the incision is a laparotomy and the tissue is fascia of the abdominal wall.

4. The suturing technique according to claim 1, wherein the first portions of the first suture thread intermittently penetrate and exit the first region of tissue along each of the rows of puncture sites while generally avoiding penetration at any of the puncture sites.

5. The suturing technique according to claim 4, wherein the first portions of the first suture thread are on sides of the rows of puncture sites proximal to the incision.

6. The suturing technique according to claim 1, wherein the continuous suture is in the tissue of the suture area and closed with a knot, and the second suture thread successively traverses the incision above and below the first region of tissue in transverse directions to the incision.

7. The suturing technique according to claim 1, wherein the first suture thread comprises second portions that are outside the first region of tissue.

8. The suturing technique according to claim 1, wherein the suture area is a first suture area, the suturing technique further comprising:
    designating an extended suture area that surrounds the first suture area, the extended suture area comprising rows of additional puncture sites that are aligned approximately parallel to the incision on opposite sides of the incision and a second region of tissue located in the extended suture area between the rows of additional puncture sites;
    using at least a third suture thread to create a second circular suture in the second region of tissue located in the extended suture area; and
    using at least a fourth suture thread to create crosslink sutures in the extended suture area that penetrate the additional puncture sites and traverse the incision;
    wherein stresses induced by tension in the crosslink sutures are dispersed by the second circular suture along the rows of additional puncture sites to an extent that tearing of the second region of tissue at each of the additional puncture sites is inhibited.

9. The suturing technique according to claim 8, the suturing technique further comprising using at least a fifth suture thread to create a third circular suture in the second region of tissue located in the extended suture area.

10. The suturing technique according to claim 1, wherein the first suture thread that creates the circular suture is a single continuous thread.

11. The suturing technique according to claim 1, wherein the second suture thread that creates the continuous suture is a single continuous thread.

\* \* \* \* \*